(12) United States Patent
da Silva Ferreira et al.

(10) Patent No.: US 8,642,333 B2
(45) Date of Patent: Feb. 4, 2014

(54) PARTICULATE DELIVERY VEHICLES FOR EMBRYOID BODIES

(75) Inventors: Lino da Silva Ferreira, Coimbra (PT); Daniel Kohane, Newton, MA (US); Robert Langer, Newton, MA (US)

(73) Assignees: Massachusetts Institute of Technology, Cambridge, MA (US); Children's Hospital Boston, Boston, MA (US)

( * ) Notice: Subject to any disclaimer, the term of this patent is extended or adjusted under 35 U.S.C. 154(b) by 804 days.

(21) Appl. No.: 12/365,604

(22) Filed: Feb. 4, 2009

(65) Prior Publication Data

US 2009/0263359 A1 Oct. 22, 2009

Related U.S. Application Data

(60) Provisional application No. 61/026,024, filed on Feb. 4, 2008.

(51) Int. Cl.
*C12N 5/00* (2006.01)
*C12N 5/02* (2006.01)

(52) U.S. Cl.
USPC ............ 435/377; 435/384; 435/383; 435/394

(58) Field of Classification Search
None
See application file for complete search history.

(56) References Cited

U.S. PATENT DOCUMENTS

| 5,942,435 | A * | 8/1999 | Wheeler ........................ 435/325 |
| 7,547,547 | B2 * | 6/2009 | Dang et al. .................... 435/382 |
| 2004/0058008 | A1 | 3/2004 | Tarcha et al. |
| 2005/0031598 | A1 | 2/2005 | Levenberg et al. |
| 2005/0255588 | A1 | 11/2005 | Young et al. |

OTHER PUBLICATIONS

Schuldiner et al 2000, PNAS, 97:11307.*
Sato et al. (2004) Nat. Med. 10:55-63.*
Humphrey et al. (2004) Stem Cells 22: 522-530.*
Verfaillie et al. Hematology, pp. 369-381, 2002.*
Hoffman et al. Nature Biotech., 23(6): 699-708, 2005.*
Ng , 2005, Blood, 106:1601-1603.*
Ferreira et al Jan. 1997, Biomaterials, 28:2706-2717.*
Ferreira 2008, Advanced Materials, 20:2285-2291.*
Simmons, 1992, Journal of Immunology, 148:267-271.*
Carpenedo, 2010, Journal of Biomedical Materials Research, 94A:466-475.*
Dang, et al. "Controlled, Scalable Embryonic Stem Cell Differentiation Culture" Stem Cells, 2004, vol. 22, pp. 275-282.
Panyam, et al. "Polymer Degradation and In Vitro Release of a Model protein from Poly(lactide-coglycolide) Nano- and Microparticles" J. of Controlled Release, 2003, vol. 92, pp. 173-187.
International Search Report for International Application Serial No. PCT/US09/033073.
Written Opinion for International Application Serial No. PCT/US09/033073.

* cited by examiner

*Primary Examiner* — Valarie Bertoglio
(74) *Attorney, Agent, or Firm* — Choate, Hall & Stewart LLP; Brenda Herschbach Jarrell; John J. Cahill

(57) ABSTRACT

The present invention provides a vehicle for delivering various chemicals, compositions and proteins to stem cells and embryoid bodies. The vehicle may be biocompatible and biodegradable polymer microparticles. Typically the particles will contain at least a growth factor for delivery to the embryoid bodies, and generally the growth factor induces differentiation of the cells in the embryoid body along a specific lineage. The present invention also provides methods for directing differentiation of the cells in the embryoid body.

12 Claims, 10 Drawing Sheets

SEQUENCE LISTING

```
<160> NUMBER OF SEQ ID NOS: 12

<210> SEQ ID NO 1
<211> LENGTH: 40
<212> TYPE: PRT
<213> ORGANISM: Artificial Sequence
<220> FEATURE:
<223> OTHER INFORMATION: Endothelial - Primer Sequence for Gene
      transcript PECAM1

<400> SEQUENCE: 1

Gly Cys Thr Gly Thr Thr Gly Gly Thr Gly Gly Ala Ala Gly Gly Ala
1               5                   10                  15

Gly Thr Gly Cys Gly Ala Ala Gly Thr Thr Gly Gly Cys Thr Gly Gly
            20                  25                  30

Ala Gly Gly Thr Gly Cys Thr Cys
        35                  40

<210> SEQ ID NO 2
<211> LENGTH: 40
<212> TYPE: PRT
<213> ORGANISM: Artificial Sequence
<220> FEATURE:
<223> OTHER INFORMATION: Endothelial - Primer Sequence for Gene
      transcript CD34

<400> SEQUENCE: 2

Thr Gly Ala Ala Gly Cys Cys Thr Ala Gly Cys Cys Thr Gly Thr Cys
1               5                   10                  15

Ala Cys Cys Thr Cys Gly Cys Ala Cys Ala Gly Cys Thr Gly Gly Ala
            20                  25                  30

Gly Gly Thr Cys Thr Thr Ala Thr
        35                  40
```

```
<210> SEQ ID NO 3
<211> LENGTH: 46
<212> TYPE: PRT
<213> ORGANISM: Artificial Sequence
<220> FEATURE:
<223> OTHER INFORMATION: Endothelial - Primer Sequence for Gene
      transcript KDR/Flk-1

<400> SEQUENCE: 3

Cys Thr Gly Gly Cys Ala Thr Gly Gly Thr Cys Thr Cys Thr Gly
1               5                   10                  15

Thr Gly Ala Ala Gly Cys Ala Ala Thr Ala Cys Cys Ala Gly Thr
                20                  25                  30

Gly Gly Ala Thr Gly Thr Gly Ala Thr Gly Gly Cys Gly Gly
            35                  40                  45

<210> SEQ ID NO 4
<211> LENGTH: 40
<212> TYPE: PRT
<213> ORGANISM: Artificial Sequence
<220> FEATURE:
<223> OTHER INFORMATION: Endothelial - Primer Sequence for Gene
      transcript Angiopoietin-2

<400> SEQUENCE: 4

Gly Gly Ala Thr Cys Thr Gly Gly Gly Ala Gly Ala Gly Ala Gly
1               5                   10                  15

Gly Ala Ala Cys Cys Ala Thr Cys Thr Gly Cys Ala Cys Gly Ala
                20                  25                  30

Thr Gly Cys Ala Thr Gly Thr Ala
            35                  40

<210> SEQ ID NO 5
<211> LENGTH: 54
<212> TYPE: PRT
<213> ORGANISM: Artificial Sequence
<220> FEATURE:
<223> OTHER INFORMATION: Endothelial - Primer Sequence for Gene
      transcript Tie-2

<400> SEQUENCE: 5

Ala Thr Cys Cys Cys Ala Thr Thr Thr Gly Cys Ala Ala Gly Cys
1               5                   10                  15

Thr Thr Cys Thr Gly Gly Cys Thr Gly Gly Cys Thr Gly Thr Ala
                20                  25                  30

Ala Gly Cys Gly Thr Cys Thr Cys Ala Cys Ala Gly Thr Cys Cys
            35                  40                  45

Ala Gly Gly Ala Thr Gly
        50

<210> SEQ ID NO 6
<211> LENGTH: 40
<212> TYPE: PRT
<213> ORGANISM: Artificial Sequence
<220> FEATURE:
<223> OTHER INFORMATION: Endothelial - Primer Sequence for Gene
      transcript  VE-cad

<400> SEQUENCE: 6

Ala Cys Gly Gly Gly Ala Thr Gly Ala Cys Cys Ala Ala Gly Thr Ala
1               5                   10                  15

Cys Ala Gly Cys Ala Cys Ala Cys Ala Cys Thr Thr Thr Gly Gly Gly
                20                  25                  30
```

Cys Thr Gly Gly Thr Ala Gly Gly
        35              40

<210> SEQ ID NO 7
<211> LENGTH: 40
<212> TYPE: PRT
<213> ORGANISM: Artificial Sequence
<220> FEATURE:
<223> OTHER INFORMATION: Endothelial - Primer Sequence for Gene
      transcript von Willebrand Factor - vWF

<400> SEQUENCE: 7

Ala Thr Gly Thr Thr Gly Thr Gly Gly Ala Gly Ala Thr Gly Thr
1               5                   10                  15

Thr Thr Gly Cys Gly Cys Ala Gly Ala Thr Ala Ala Gly Ala Gly Cys
            20                  25                  30

Thr Cys Ala Gly Cys Cys Thr Thr
        35              40

<210> SEQ ID NO 8
<211> LENGTH: 39
<212> TYPE: PRT
<213> ORGANISM: Artificial Sequence
<220> FEATURE:
<223> OTHER INFORMATION: Glyceraldehyde 3-phosphate dehydrogenase Primer
      Sequence for Gene transcript GAPDH

<400> SEQUENCE: 8

Ala Gly Cys Cys Ala Cys Ala Thr Cys Gly Cys Thr Cys Ala Gly Ala
1               5                   10                  15

Cys Ala Cys Cys Gly Thr Ala Cys Thr Cys Ala Gly Cys Gly Cys Cys
            20                  25                  30

Ala Gly Cys Ala Thr Cys Gly
        35

<210> SEQ ID NO 9
<211> LENGTH: 44
<212> TYPE: PRT
<213> ORGANISM: Artificial Sequence
<220> FEATURE:
<223> OTHER INFORMATION: Neuronal - Primer Sequence for Gene transcript
      Neurofilament 68Kd

<400> SEQUENCE: 9

Gly Ala Gly Thr Gly Ala Ala Ala Thr Gly Gly Cys Ala Cys Gly Ala
1               5                   10                  15

Thr Ala Cys Cys Thr Ala Thr Thr Thr Cys Cys Thr Cys Thr Cys Cys
            20                  25                  30

Thr Thr Cys Thr Thr Cys Ala Cys Cys Thr Thr Cys
        35              40

<210> SEQ ID NO 10
<211> LENGTH: 38
<212> TYPE: PRT
<213> ORGANISM: Artificial Sequence
<220> FEATURE:
<223> OTHER INFORMATION: Neuronal - Primer Sequence for Gene transcript
      Nestin

<400> SEQUENCE: 10

Ala Gly Ala Gly Gly Gly Gly Ala Ala Thr Thr Cys Cys Thr Gly Gly
1               5                   10                  15

Ala Gly Cys Thr Gly Ala Gly Gly Ala Cys Cys Ala Gly Gly Ala Cys
            20                  25                  30

-continued

```
Thr Cys Thr Cys Thr Ala
        35

<210> SEQ ID NO 11
<211> LENGTH: 48
<212> TYPE: PRT
<213> ORGANISM: Artificial Sequence
<220> FEATURE:
<223> OTHER INFORMATION: Hepatocyte - Primer Sequence for Gene
      transcript Albumin

<400> SEQUENCE: 11

Thr Gly Cys Thr Thr Gly Ala Ala Thr Gly Thr Gly Cys Thr Gly Ala
1               5                   10                  15

Thr Gly Ala Cys Ala Gly Gly Gly Ala Ala Gly Gly Cys Ala Ala Gly
            20                  25                  30

Thr Cys Ala Gly Cys Ala Gly Cys Cys Ala Thr Cys Thr Cys Ala Thr
        35                  40                  45

<210> SEQ ID NO 12
<211> LENGTH: 50
<212> TYPE: PRT
<213> ORGANISM: Artificial Sequence
<220> FEATURE:
<223> OTHER INFORMATION: Hepatocyte - Primer Sequence for Gene
      transcript alpha-fetoprotein

<400> SEQUENCE: 12

Gly Cys Thr Gly Gly Ala Thr Thr Gly Thr Cys Thr Gly Cys Ala Gly
1               5                   10                  15

Gly Ala Thr Gly Gly Gly Gly Ala Ala Thr Cys Cys Cys Cys Thr Gly
            20                  25                  30

Ala Ala Gly Ala Ala Ala Ala Thr Thr Gly Gly Thr Thr Ala Ala Ala
        35                  40                  45

Ala Thr
    50
```

US 8,642,333 B2

PARTICULATE DELIVERY VEHICLES FOR EMBRYOID BODIES

This application claims priority to U.S. Provisional Application No. 61/026,024, filed Feb. 4, 2008, the entire contents of which is incorporated herein by reference.

GOVERNMENT SUPPORT

The United States Government has provided grant support utilized in the development of one or more of the present inventions. In particular, National Institute of Health (NIH) contract numbers HL060435, DE13023 and HL076485 have supported development of one or more of the inventions of the present application. The United States Government may have certain rights in these inventions.

BACKGROUND

During normal embryogenesis, human embryonic stem cells (hESCs) differentiate along different lineages in the context of complex three-dimensional tissue structures where various growth factors direct the differentiation process at different times. Embryoid bodies (EBs) are frequently used as a means to achieve specific stages of embryogenesis in vitro [1-5]. They can be formed from hESC aggregates removed from a feeder layer and cultured in suspension (termed regular EBs). EBs allow cell-cell interaction and they can be rapidly expanded to yield differentiated cells by the use of bioreactors [6,7]. Because of heterogeneous size and spontaneous differentiation of EBs into the three germ layers of the embryo including ectoderm, mesoderm and endoderm [1], it is generally difficult to control their differentiation. Vascular cells are very promising for tissue engineering applications and the treatment of cardiovascular diseases such as myocardial ischemia [22].

SUMMARY OF INVENTION

In various aspect the present invention encompasses a method of directing differentiation of stem cells including the steps of, providing stem cells, providing a microparticle wherein the microparticle comprises a growth factor, contacting the stem cells with the microparticles under conditions suitable to effect differentiation of the cells of the embryoid bodies; and centrifuging the mixture of cells and microparticles.

In various embodiments, the method includes particles made from a bio-compatible and biodegradable polymer. In various embodiments, the polymer is selected from poly(anhydrides), poly(hydroxy acids), poly(ortho esters), poly(propylfumerates), poly(caprolactones), polyamides, polyamino acids, polyacetals, biodegradable polycyanoacrylates, biodegradable polyurethanes, poly(glycerol sebacates), elastomeric poly(glycerol sebacates polysaccharides), and combinations thereof. In various embodiments, the polymer is selected from polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers and combinations thereof. In various embodiments, the polymer is poly(lactide-co-glycolide) (PLGA).

In various embodiments, the cells express CD 34. In various embodiments, the cells express PECAM1.

In various embodiments, the particles have a mean size in the range between about 0.2 μm and about 25 μm. In various embodiments, the particles include growth factors, proteins, small chemicals, DNA, RNA, RNAi and combinations thereof. In various embodiments, the growth factor is selected from the group comprising vascular endothelial growth factor (VEGF165), basic fibroblast growth factor (bFGF), placenta growth factor (PlGF), and combinations thereof.

In various embodiments, the growth factor is selected from the group comprising epidermal growth factor, nerve growth factor, transforming growth factor-β, platelet-derived growth factor, insulin-like growth factor, acidic fibroblast growth factor, basic fibroblast growth factor, hepatocyte growth factor, brain-derived neurotrophic factor, keratinocyte growth factor, bone morphogenetic protein, a cartilage-derived growth factor, and combinations thereof.

In various embodiments, the cells are selected from human stem cells, embryonic stem cells or adult stem cells.

In various embodiments, the particles are taken up by the cells in the embryoid bodies. In various embodiments, the particles are not take up by the cells in the embryoid bodies.

In various embodiments, the differentiation of the cells is toward the mesoderm, endoderm, or ectoderm layer. In various embodiments, the differentiation of the cells is away from the endoderm or the ectoderm layer. In various embodiments, the differentiation of the cells is toward mesenchymal cells, endothelial cells, vascular cells, neuronal or hepatic cells In various embodiments, about 30,000 cells are provided.

In various aspects, the present invention encompasses compositions including embryoid bodies, and microparticles wherein the microparticles comprise a polymer and a growth factor in a solution comprising a differentiation medium. In various embodiments, the composition further includes a different medium.

In various embodiments, the particles made from a biocompatible and biodegradable polymer. In various embodiments, the polymer is poly(lactide-co-glycolide) (PLGA). In various embodiments, the particles have a mean size in the range between about 0.2 μm and about 25 μm.

In various embodiments, the particles include growth factors, proteins, small chemicals, DNA, RNA, RNAi and combinations thereof. In various embodiments, the growth factor is selected from the group comprising vascular endothelial growth factor (VEGF165), basic fibroblast growth factor (bFGF), placenta growth factor (PlGF), and combinations thereof. In various embodiments, the microparticles all have the same release profile, or different release profiles. In various embodiments, the particles are fluorescent, magnetic, or fluorescent and release growth factors. In various embodiments, the composition includes a mixture of different growth factor containing particles with embryoid bodies.

In various embodiments, the particles are taken up by the cells in the embryoid bodies. In various embodiments, the particles are not take up by the cells in the embryoid bodies.

In various embodiments, the differentiation of the cells is toward the mesoderm.

In various aspects, the present invention includes a of directing differentiation of cells of embryoid bodies including the steps of providing embryoid bodies, providing microparticles wherein the microparticles comprise VEGF165, bFGF or PlGF, and contacting the embryoid bodies with the microparticles under conditions suitable to effect differentiation of the cells of the embryoid bodies, wherein the cells comprising the embryoid bodies differentiate toward vascular cells.

In various aspects and various embodiments the present inventions provide methods for the differentiation of hESCs by the incorporation of growth factor-releasing particles in EBs. In various embodiments, a methodology can facilitate the control of the differentiation of hESCs into a vascular lineage. In various aspects, various embodiments of the present inventions provide methods for delivery of growth factors to embryoid bodies. In various embodiments, the present inventions facilitate enhancing the differentiation of embryoid bodies. In various embodiments the cell viability of EBs after the incorporation of these particles is over 80%. In various embodiments, the effect on vascular differentiation of particles containing growth factors was improved relative to that observed by exposing EBs to extrinsic doses of the same growth factors.

In various embodiments, the particles are comprised of a polymer. In various embodiments the polymer is a biodegradable and biocompatible polymer. In various embodiments of the present inventions particles of a bio-compatible, biodegradable polymer are generated to have a mean size of about 25 µm, about 6 µm or about 0.24 µm. In various embodiments of the present inventions the polymer is PLGA. In various embodiments of the present inventions the particles are made in a solution containing growth factors. In various embodiments of the present inventions embryoid bodies containing the particles where prepared by seeding hESCs in a solution containing particles, followed by agitation by centrifuge.

Various embodiments of the present inventions facilitate control of several variables of potential importance for cell differentiation including growth factor concentration, spatial positioning of growth factor and combinatorial release of bioactive molecules are controlled. In various embodiments of the present inventions the particle solution contains about 0.15 mg of particles per mL of differentiation medium, or about 0.06 mg of particles per mL of differentiation medium.

In various embodiments the various particles experienced intracellular transport. In various embodiments particles are taken up by hESCs and accumulate in the perinuclear region.

In various embodiments of the present inventions the particles were taken up by the embryoid bodies in about greater than or equal to 13% of cells and in various aspects, the particles were taken up by about 90% of the cells in the EBs. In various aspects the particles were taken up by the embryoid bodies and located intracellularly. In various aspects the particles taken up by the cells were located in the perinuclear region of the cell. In various aspects the particles were extracellular, not taken up by the cells.

In various embodiments of the present inventions, the incorporation of particulate growth factor-delivery vehicles in EBs facilitates enhancing vascular differentiation of the EBs by increasing the growth factor concentration within the EBs, potentially at doses and in time frames determined by the method of manufacture of both the particles and EBs. In various embodiments, the local delivery of growth factors within these 3D cellular structures facilitates extending the duration of exposure of cells to the growth factors, which otherwise tend to have short half-lives [8]. Previously, nerve growth factor-releasing particles assembled with fetal brain cells have been reported to enhance cell survival and functionality; however, the role of these particles in cell differentiation was unclear [9]. In various embodiments, incorporating particles with EBs facilitates implantation of both the cells and the drug delivery system together and subsequently they remain together after placement in vivo.

In various embodiments of the present inventions, the differentiated embryoid bodies favored differentiation toward endothelial and endothelial progenitor cells. In various embodiments of the present inventions the differentiated embryoid bodies underwent vascular differentiation. In various embodiments of the present inventions the differentiated embryoid bodies differentiated toward the mesoderm germ layer over the ectoderm germ layer or the endoderm germ layer.

BRIEF DESCRIPTION OF THE DRAWINGS

The foregoing and other aspects, embodiments, objects, features and advantages of the present inventions can be more fully understood from the following description in conjunction with the accompanying drawings. In the drawings, like reference characters generally refer to like features and structural elements through the various Figures. The drawings are not necessarily to scale, emphasis instead being placed up on illustrating the principles of the present inventions, where.

DETAILED DESCRIPTION OF VARIOUS EMBODIMENTS

Figure 1:
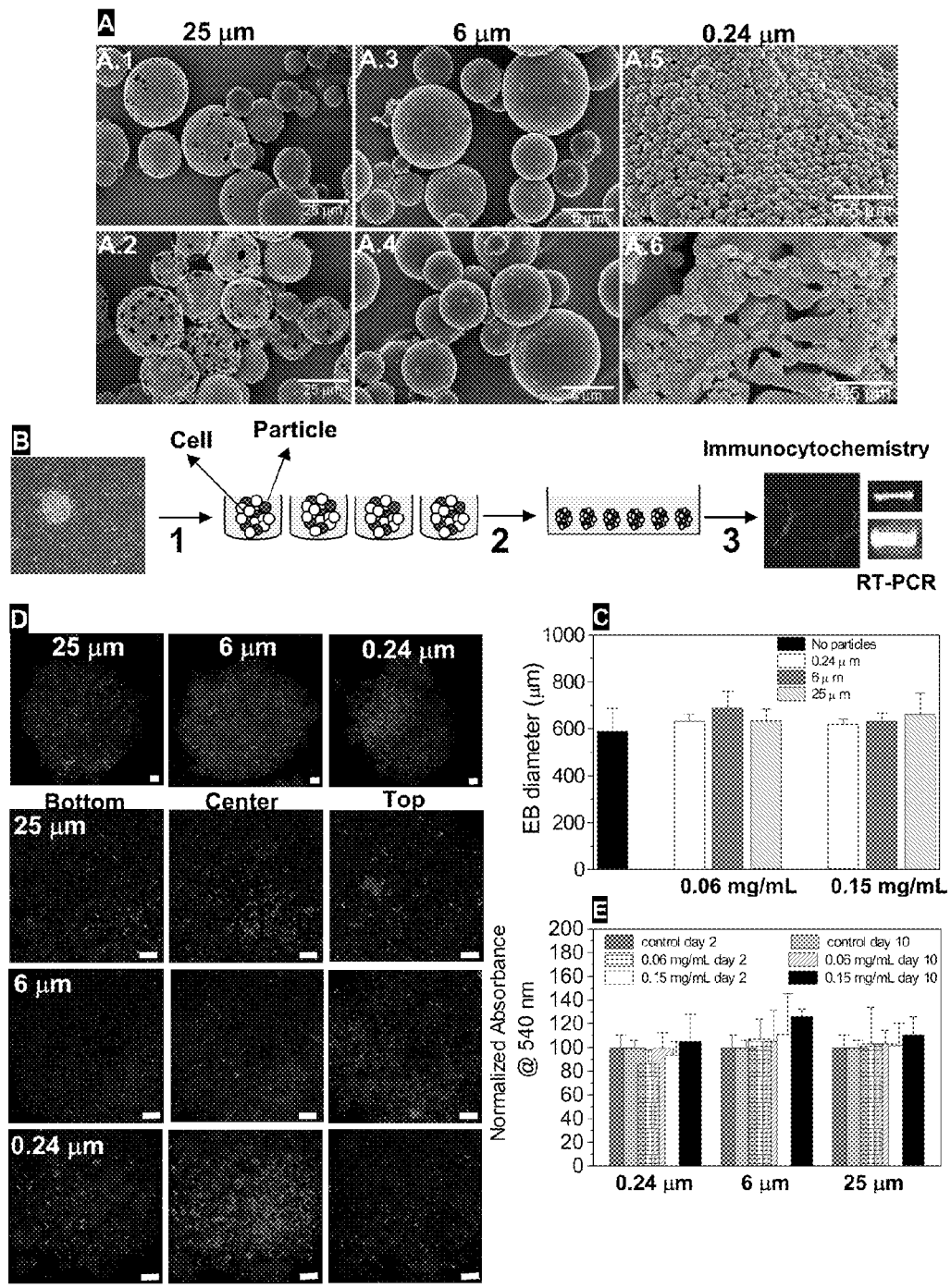
FIG. 1 illustrates preparation and viability of EBs containing particles. A) Scanning electron microscopy of particles 25 µm (A.1, A.2), 6 µm (A.3, A.4) and 0.24 µm (A.5, A.6) at day 0 (A.1, A.3, A.5) and 10 (A.2, A.4, A.6), after incubation in PBS at 37° C. B) Scheme for the formation of EBs containing particles. (1) Undifferentiated hESC colonies were dissociated into single cells which were aggregated with particles of different sizes in a 96 well-plate by centrifugation forming EBs. (2) After 2 days, EBs were transferred to a low adhesion 24-well plate and cultured for additional 8 days in differentiation medium. (3) EBs were then characterized by immunocytochemistry and quantitative RT-PCR. C) Size of EBs (average±S.D., n=13) formed by the aggregation of 30,000 cells in the presence or absence of different concentrations of PLGA particles. D) Distribution of TRITC-labeled particles with different sizes in EBs at different depths, as evaluated by confocal microscopy. EBs were formed by the aggregation of 30,000 hESCs and 0.15 mg/mL of particles. Bar corresponds to 100 µm. E) Mitochondrial metabolic activity (average±S.D., n=6) of EBs formed by the aggregation of 30,000 hESCs and different concentrations of particles with different size, at day 2 and 10. The absorbances at 540 nm were normalized by control day 2 absorbance.

In the present application, methods for directing differentiation of embryoid bodies to a type of tissue by using particles to deliver growth factors to the embryoid bodies are provided. In various embodiments, differentiation is directed to a vascular lineage.

The following definitions may be useful in understanding embryoid bodies, differentiation and tissue engineering materials.

"Bioactive agents": As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, and imaging agents. In certain embodiments, the bioactive agent is a drug.

A more complete listing of bioactive agents and specific drugs suitable for use in the present invention may be found in "Pharmaceutical Substances: Syntheses, patents, applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

By "biocompatible" is meant to describe materials that do not elicit an undesirable detrimental response in contact with cells.

By "biodegradable" is meant to describe polymers that degrade fully (i.e., down to monomeric species) under physiological or endosomal conditions. In preferred embodiments, the polymers and polymer biodegradation byproducts are biocompatible. Biodegradable polymers are not necessarily hydrolytically degradable and may require enzymatic action to fully degrade.

"Vascular progenitor cells" refers to a population of cells that can generate progeny that are endothelial or smooth muscle precursors (such as angioblasts) or mature endothelial or smooth muscle cells, or hematopoietic precursor (such as erythroid colony forming units and megakaryocytes) or mature blood cells (such as erythrocytes and leukocytes). Vascular progenitor cells may express some of the phenotypic markers that are characteristic of the endothelial, smooth muscle and hematopoietic lineages. Vascular progenitor cells include EL, SML, and HL.

"Endothelial like cells" refers to cells that can themselves or whose progeny can differentiate into mature endothelial cells. These cells may, but need not, have the capacity to generate hematopoetic or smooth muscle cells.

By "undifferentiated" is meant to describe when a substantial portion of stem cells and their derivatives in the population display morphological characteristics of undifferentiated cells, clearly distinguishing them from differentiated cells of embryonic or adult origin. Undifferentiated embryonic stem cells are easily recognized by microscopic view as cells with high nuclear/cytoplasm ratios and prominent nucleoli. Similarly, undifferentiated cells can be distinguished from differentiated cells by the expression of one or more of the following stem cell markers: SSEA-4, TRA-1-60, TRA-1-81, Nanog and alkaline phosphatase. Human embryonic stem cells also express surface antigens initially described in other stem cell populations such as AC133, c-kit (CD177), flt3 (CD135) and CD9.

As used herein, "growth factors" are chemicals that regulate cellular metabolic and/or signaling processes, including but not limited to differentiation, proliferation, synthesis of various cellular products, and other metabolic activities.

Figure 5:
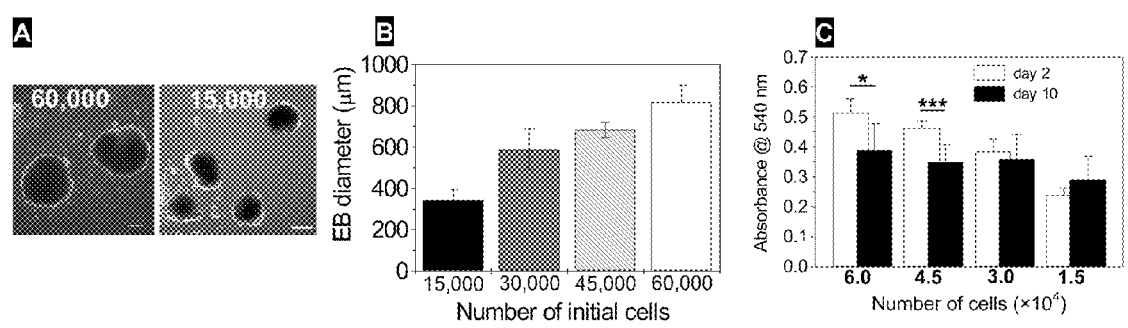
FIG. 5 illustrates EB size and metabolic activity. A) Images of EBs at day 2 of differentiation, without particles, obtained by the forced aggregation of 60,000 and 15,000 hESCs. Bar corresponds to 200 μm. B) EB diameter as a function of initial cell number (average±S.D., n=20). The quantification was performed at day 2 of differentiation. C) Metabolic activity (average±S.D., n=6) of EBs formed by the aggregation of different number of hESCs at day 2 and 10. * and *** denote statistical significance (P<0.05 and P<0.001, respectively).

In various embodiments methods of preparing embryoid bodies from hESCs are provided. EBs of a range of sizes were formed by depositing between about 15,000 and about 60,000 hESCs in round-bottomed, low adherence, 96 well plates and aggregated by centrifugation (FIG. 1A) [10]. EBs with diameters between about 340 and about 820 μm were obtained by changing the initial seeding number of cells (FIG. 5). EBs formed by about 15,000 to about 30,000 cells showed no comparatively consistent metabolic activity as measured by a MTT assay for about 10 days when compared to a decrease in metabolic activity that was observed for EBs formed by a deposition of more than about 30,000 cells (FIG. 5). In various embodiments, embryoid bodies consisting of about 30,000 cells are used and differentiated in suspension for about 10 days based on previous results in the differentiation of hESCs into a vascular lineage [2].

In various embodiments of the present inventions, particles are provided as a system to design growth factor-releasing systems (FIG. 1B and Table 1).

TABLE 1

Characteristics of blank-PLGA particles.

| Characteristics | Blank- PLGA particles | | |
| --- | --- | --- | --- |
| | Nano | 6 μm | 25 μm |
| Polymer inherent viscosity (dl/g) [a] | 0.16-0.24 | 0.16-0.24 | 0.32-0.44 |
| Encapsulated molecules [b] | BSA-Heparin-$MgOH_2$ | BSA-Heparin-$MgOH_2$ | BSA-Heparin-$MgOH_2$-sucrose |
| Particle size (μm) [c] | 0.239 ± 0.002 | 6.14 ± 2.74 | 25.08 ± 16.30 |
| Polydispersity [c] | 0.222 | NA | NA |

[a] Information obtained by the manufacturer.
[b] 2.5 mg of BSA, 5 μg of heparin, 4 mg of $MgOH_2$ and 4 mg of sucrose were used per 100 mg of polymer.
[c] For nanoparticles: particle size and polydispersity measurements were measured by using a ZetaPALS dynamic light scattering detector (Brookhaven Instruments Corp., Holtsville, NY, 15-mW laser, incident beam 676 nm). For microparticles: particle size was measured by a Coulter microparticle analyzer (Multisizer 3, Beckman Coulter, Miami, FL) (sample count: 50,000 microparticles).

Growth factors may include several families of, chemicals, including but not limited to cytokines, eicosanoids, and differentiation factors.

By "small molecule" is meant to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§. 500 through 589, incorporated herein by reference, are all considered acceptable for use in accordance with the present invention.

"Tissue": as used herein, the term "tissue" refers to a collection of cells of one or more types combined to perform a specific function, and any extracellular matrix surrounding the cells.

In various aspects the methods of the present invention comprise the steps of preparing embryoid bodies from hESCs, preparing particles in a range of sizes, incorporating the particles with solutions containing growth factors, incorporating the embryoid bodies in solution with growth factor delivering particles.

In general, a particle in accordance with the present invention has a greatest dimension (e.g. diameter) of less than 1000 microns (μm). In some embodiments, inventive particles have a greatest dimension of less than 10 μm. In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 300 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm. In some embodiments, inventive particles have a greatest dimension ranging between 50 nm and 100 nm. In some embodiments, inventive particles have a greatest dimension ranging between 10 nm and 100 nm.

In some embodiments, particles have a diameter of approximately 1000 nm. In some embodiments, particles have a diameter of approximately 750 nm. In some embodiments, particles have a diameter of approximately 500 nm. In some embodiments, particles have a diameter of approximately 450 nm. In some embodiments, particles have a diameter of approximately 400 nm. In some embodiments, particles have a diameter of approximately 350 nm. In some embodiments, particles have a diameter of approximately 300 nm. In some embodiments, particles have a diameter of approximately 275 nm. In some embodiments, particles have a diameter of approximately 250 nm. In some embodiments, particles have a diameter of approximately 225 nm. In some embodiments, particles have a diameter of approximately 200 nm. In some embodiments, particles have a diameter of approximately 175 nm. In some embodiments, particles have a diameter of approximately 150 nm. In some embodiments, particles have a diameter of approximately 125 nm. In some embodiments, particles have a diameter of approximately 100 nm. In some embodiments, particles have a diameter of approximately 75 nm. In some embodiments, particles have a diameter of approximately 50 nm. In some embodiments, particles have a diameter of approximately 25 nm.

In certain embodiments, particles are greater in size than the renal excretion limit (e.g. particles having diameters of greater than 6 nm). In certain embodiments, particles are small enough to avoid clearance of particles from the bloodstream by the liver (e.g. particles having diameters of less than 1000 nm). In general, physiochemical features of particles should allow a targeted particle to circulate longer in plasma by decreasing renal excretion and liver clearance.

It is often desirable to use a population of particles that is relatively uniform in terms of size, shape, and/or composition so that each particle has similar properties. For example, at least 80%, at least 90%, or at least 95% of the particles may have a diameter or greatest dimension that falls within 5%, 10%, or 20% of the average diameter or greatest dimension. In some embodiments, a population of particles may be heterogeneous with respect to size, shape, and/or composition.

In some embodiments, particles may optionally comprise one or more surfactants. In some embodiments, a surfactant can promote the production of particles with increased stability, improved uniformity, or increased viscosity. Surfactants can be particularly useful in embodiments that utilize two or more dispersion media. The percent of surfactant in particles can range from 0% to 99% by weight, from 10% to 99% by weight, from 25% to 99% by weight, from 50% to 99% by weight, or from 75% to 99% by weight. In some embodiments, the percent of surfactant in particles can range from 0% to 75% by weight, from 0% to 50% by weight, from 0% to 25% by weight, or from 0% to 10% by weight. In some embodiments, the percent of surfactant in particles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

Any surfactant known in the art is suitable for use in making particles in accordance with the present invention. Such surfactants include, but are not limited to, phosphoglycerides; phosphatidylcholines; dipalmitoyl phosphatidylcholine (DPPC); dioleoylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); 1,2-distearoyl-sn-glycero-3-phosphoethanolamine (DSPE); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span 85) glycocholate; sorbitan monolaurate (Span 20); polysorbate 20 (Tween-20); polysorbate 60 (Tween-60); polysorbate 65 (Tween-65); polysorbate 80 (Tween-80); polysorbate 85 (Tween-85); polyoxyethylene monostearate; surfactin; a poloxamer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. The surfactant component may be a mixture of different surfactants. These surfactants may be extracted and purified from a natural source or may be prepared synthetically in a laboratory. In certain specific embodiments, surfactants are commercially available.

Those skilled in the art will recognize that this is an exemplary, not comprehensive, list of substances with surfactant activity. Any surfactant may be used in the production of particles to be used in accordance with the present invention.

Lipids

In some embodiments, particles may optionally comprise one or more lipids. The percent of lipid in particles can range from 0% to 99% by weight, from 10% to 99% by weight, from 25% to 99% by weight, from 50% to 99% by weight, or from 75% to 99% by weight. In some embodiments, the percent of lipid in particles can range from 0% to 75% by weight, from 0% to 50% by weight, from 0% to 25% by weight, or from 0% to 10% by weight. In some embodiments, the percent of lipid in particles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

In some embodiments, lipids are oils. In general, any oil known in the art can be included in particles. In some embodiments, an oil may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid group may be a $C_{15}$-$C_{25}$ fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In some embodiments, the oil is a liquid triglyceride.

Suitable oils for use with the present invention include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, and combinations thereof. Suitable oils for use with the present invention include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In some embodiments, a lipid is a hormone (e.g. estrogen, testosterone), steroid (e.g., cholesterol, bile acid), vitamin (e.g. vitamin E), phospholipid (e.g. phosphatidyl choline), sphingolipid (e.g. ceramides), or lipoprotein (e.g. apolipoprotein).

Carbohydrates

In some embodiments, particles may optionally comprise one or more carbohydrates. The percent of carbohydrate in particles can range from 0% to 99% by weight, from 10% to 99% by weight, from 25% to 99% by weight, from 50% to 99% by weight, or from 75% to 99% by weight. In some embodiments, the percent of carbohydrate in particles can range from 0% to 75% by weight, from 0% to 50% by weight, from 0% to 25% by weight, or from 0% to 10% by weight. In some embodiments, the percent of carbohydrate in particles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

Carbohydrates may be natural or synthetic. A carbohydrate may be a derivatized natural carbohydrate. In certain embodiments, a carbohydrate is a monosaccharide, including but not limited to glucose, fructose, galactose, ribose, lactose, sucrose, maltose, trehalose, cellobiose, mannose, xylose, arabinose, glucoronic acid, galacturonic acid, mannuronic acid, glucosamine, galactosamine, and neuramic acid. In certain embodiments, a carbohydrate is a disaccharide, including but not limited to lactose, sucrose, maltose, trehalose, and cellobiose. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucomannan, pustulan, heparin, hyaluronic acid, curdlan, and xanthan. In certain embodiments, the carbohydrate is a sugar alcohol, including but not limited to mannitol, sorbitol, xylitol, erythritol, maltitol, and lactitol.

Particles can be solid or hollow and can comprise one or more layers (e.g., nanoshells, nanorings). In some embodiments, each layer has a unique composition and unique properties relative to the other layer(s). To give but one example, particles may have a core/shell structure, wherein the core is one layer and the shell is a second layer. In certain embodiments, only the shell is biodegradable. In certain other embodiments, both the core and shell are biodegradable. The core and shell may have different rates of degradation. Particles may comprise a plurality of different layers. In some embodiments, one layer may be substantially cross-linked, a second layer is not substantially cross-linked, and so forth. In some embodiments, one, a few, or all of the different layers may comprise one or more agents to be delivered. In some embodiments, one layer comprises an agent to be delivered, a second layer does not comprise an agent to be delivered, and so forth. In some embodiments, each individual layer comprises a different agent or set of agents to be delivered. In certain embodiments, the radiopharmaceutical agent is attached to or included within the outer shell. In other embodiments, the radiopharmaceutical agent is included within the core of the particle. In other embodiments, the non-radioactive agent is included with the outer shell or associated with the outer shell. In certain embodiments, the non-radioactive agent is associated with the core of the particle.

In certain embodiments of the invention, a particle is porous, by which is meant that the particle contains holes or channels, which are typically small compared with the size of a particle. For example a particle may be a porous silica particle, e.g., a mesoporous silica nanoparticle or may have a coating of mesoporous silica (Lin et al., 2005, *J. Am. Chem. Soc.*, 17:4570). Particles may have pores ranging from about 1 nm to about 50 nm in diameter, e.g., between about 1 and 20 nm in diameter. Between about 10% and 95% of the volume of a particle may consist of voids within the pores or channels.

Particles may have a coating layer. Use of a biocompatible coating layer can be advantageous, e.g., if the particles contain materials that are toxic to cells. Suitable coating materials include, but are not limited to, natural proteins such as bovine serum albumin (BSA), biocompatible hydrophilic polymers such as polyethylene glycol (PEG) or a PEG derivative, phospholipid-(PEG), silica, lipids (e.g., 1,2-distearoyl-sn-glycero-3-phosphoethanolamine sodium salt (DSPE)), polymers, carbohydrates such as dextran, other nanoparticles that can be associated with inventive nanoparticles etc. Coatings may be applied or assembled in a variety of ways such as by dipping, using a layer-by-layer technique, by self-assembly, conjugation, etc. Self-assembly refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties. In certain embodiments, a lipid monolayer is self-assembled on the outside of the polymeric core of the particle. The tails of the lipid molecule associate with hydrophobic surface of the polymeric core.

In some embodiments, particles may optionally comprise one or more dispersion media, surfactants, or release-retarding ingredients. In some embodiments, particles may optionally comprise one or more plasticizers or additives.

In various aspects, particles are comprised of polymeric materials, in various aspects the particles are comprised of biocompatible and biodegradable materials. Biodegradable polymers are well known in the art and include but are not limited to collagen-GAG, collagen and fibrin. Additional biodegradable materials include, but are not limited to poly(anhydrides), poly(hydroxy acids), poly(ortho esters), poly(propylfumerates), poly(caprolactones), polyamides, polyamino acids, polyacetals, biodegradable polycyanoacrylates, biodegradable polyurethanes, poly(glycerol sebacates), elastomeric poly(glycerol sebacates), and polysaccharides. Non-biodegradable polymers may also be used as well. Other non-biodegradable, yet biocompatible polymers include, but are not limited to polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, and poly(ethylene oxide). Those skilled in the art will recognize that this is not a comprehensive, list of polymers appropriate for tissue engineering applications.

In various aspects, the particles are comprised of biocompatible and biodegradable poly(lactide-co-glycolide) (PLGA). The microparticles are substantially solid. Further the microparticles are not liposomes. In various aspects the particles are prepared to have different ranges of different sizes. In various embodiments, the morphology and degradation of particles at physiologic pH (in PBS with a pH of about 7.4) was evaluated after 10 days. In various embodiments of the present inventions, after about 10 days in phosphate buffer solution ("PBS"), particles with a mean size of about 6 μm retained their initial surface morphology while the surface of particles with a mean size of about 25 μm underwent degradation. Particles with a mean size of about 0.24 μm showed substantial aggregation and disruption of their spheroid geometry compared to the larger particles.

The particles may further include a coating including an agent that promotes cell adhesion, for example, fibronectin, integrins, or oligonucleotides that promote cell adhesion. The cells may be combined with growth-factor reduced Matrigel. The particles may further include a gel that coats internal and external surfaces of the particles, e.g., collagen gel, alginate, agar, growth factor-reduced Matrigel, and MATRIGEL™. The gel may further include one or more of laminin, fibrin, fibronectin, proteoglycans, glycoproteins, glycosaminoglycans, chemotactic agents In various embodiments of the present inventions provide methods of incorporating the particles in embryoid bodies. In general, the methods of incorporation comprise: (i) depositing about 30,000 hESCs and different concentrations of particles (about 0.15 and about 0.06 mg of particles per mL of differentiation medium) in solution and (ii) forcing their aggregation by centrifugation (FIG. 1A). At day about 2, the diameters of the EBs incorporating different particle sizes were comparatively, substantially similar (n=13, P>0.05) to the diameters of EBs made without particles (FIG. 1C). EBs were transferred at about day 2 to a second vessel in order to remove the particles that were not incorporated (about 20-30%) (FIG. 1A). Particles were distributed across the constructs with higher frequency in the center (FIG. 1D). Particles with a mean size of about 6 μm and particles with a mean size of about 0.24 μm showed aggregation in EBs. Particles with a mean size of about 20 μm particles did not show aggregation to in EBs.

Figure 6:
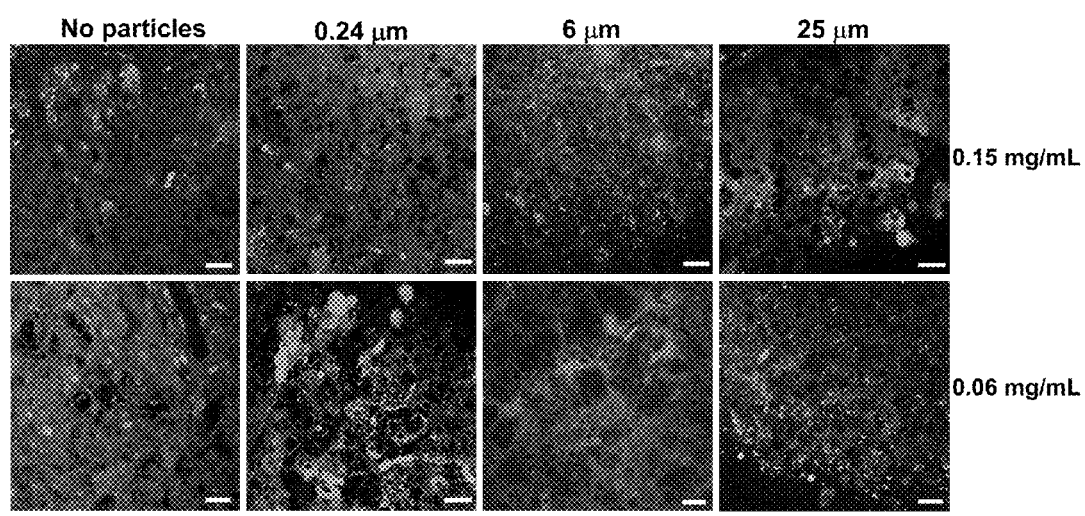
FIG. 6 illustrates cell viability in EBs formed in the presence or absence of particles with different sizes, as assessed by a LIVE/DEAD assay. The assay was performed at day 2 (n=3). Representative image for each condition is shown. Living cells fluoresce green whereas dead cells fluoresce red. Bar corresponds to 50 μm.

In various embodiments of the present inventions methods for measuring the cytotoxicity of the particles incorporated with the embryoid bodies are provided. In general the method uses a Live-Dead assay after about 2 days of EB formation. In various aspects, cell viability is above about 80 (FIG. 6).

In various embodiments, the present inventions provide methods of measuring the metabolic activity of the embryoid bodies. In general the methods comprise conducting an MTT assay. In various embodiments, as assessed by a MTT assay at about day 2, the metabolic activity in EBs with particles is substantially similar (n=6, P>0.05), in comparison to the metabolic activity in EBs without particles (FIG. 1E). In various aspects, the EBs with particles displayed cellular metabolic activity is substantially consistent, in comparison, (n=6, P>0.05) over 10 days (FIG. 1E). In various embodiments of the present inventions, EBs are in a substantially non-proliferative state, conducive to differentiation.

Figure 2:
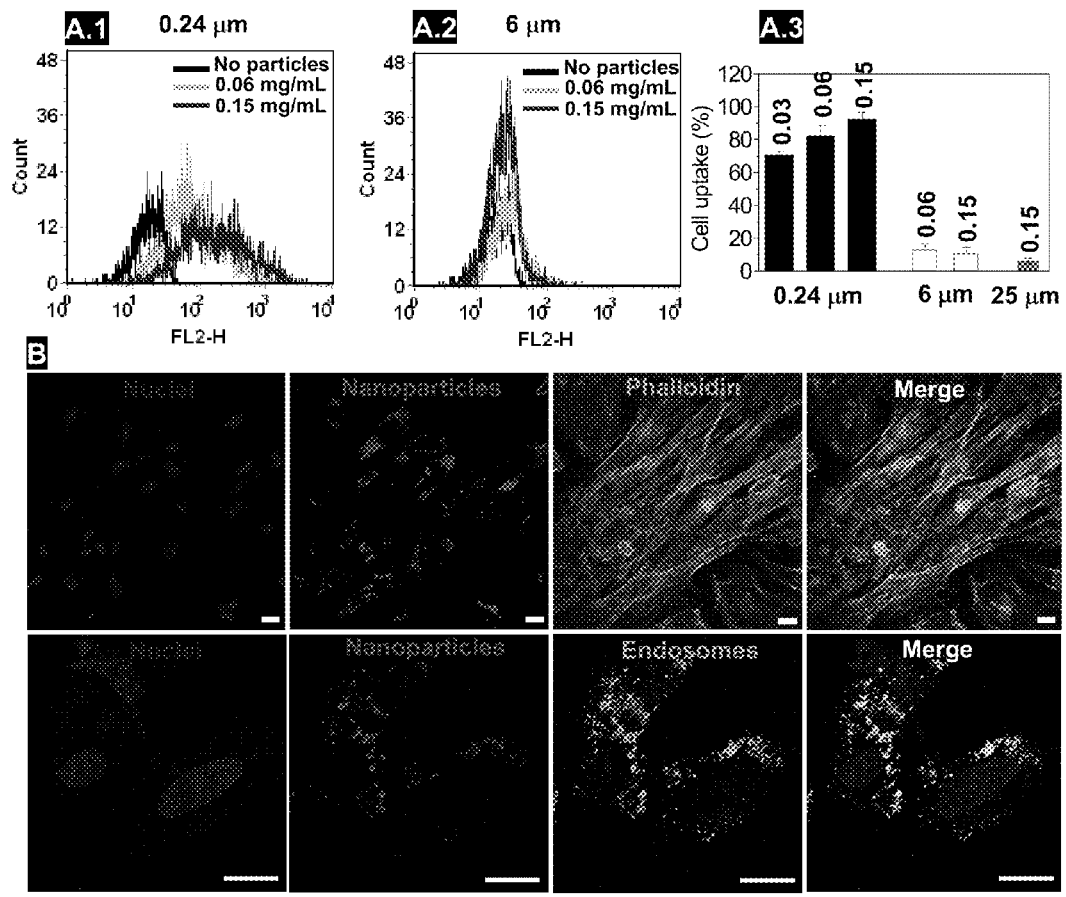
FIG. 2 illustrates cellular uptake of particles. EBs were formed by the aggregation of 30,000 hESCs and 0.15 mg/mL of particles. A) Flow cytometry analyzes of particle uptake. Quantification of TRITC-positive cells indicated that minimal cellular uptake of particles is observed for particles 6 and 25 µm in size, while substantial cellular uptake is observed for nanoparticles. B) Confocal microscopy of cellular uptake of nanoparticles. Blue Topro-3 stains the nucleus, green lysosensor indicates endosomes, green phalloidin indicates cytoplasm, and TRITC-labeled nanoparticles are displayed in red. Nanoparticles can be seen co-localized with endosomes as a yellow color and distributed mainly in the perinuclear region. For all pictures, bar corresponds to 20 µm.

Various embodiments of the present inventions provide methods for analyzing how particles are internalized by receptor-mediate endocytosis by some cell types. In general, the method comprises the steps of: (i) labeling the particles with tetramethylrhodamine-5-(and-6)-isothiocyanate (TRITC), (ii) creating a solution of the particles at a concentration of between about 0.03 mg/mL and 0.15 mg/mL, (iii) incorporating embryoid bodies in solution with particles, (iv) dissociating the cells after about 2 days, (v) plating the cells for about 18 hours, (vi) washing the plate and (vii) characterizing the uptake of the labeled particles by Fluorescence Activated Cell Sorting (FACS) (FIG. 2A). In various embodiments, particles with a mean size of about 0.24 μm (nanoparticles) were taken up by cells. In various aspects, increasing the initial dose of nanoparticles in EBs resulted in an increase in the mean fluorescence intensity as well as an increased fraction of the cell population associated with the fluorescence, indicative of particles within the cells (FIG. 2A). At the dose of about 0.15 mg/mL, over about 90% of the population was positive for the nanoparticles. The particles with a mean size of about 6 μm and the particles with a mean size of about 25 μm (microparticles) were taken up by cells at lower rate when compared to the particles with a mean size of about 0.24 μm. In various embodiments about 13% of the cell population was positive for the particles.

Figure 7:
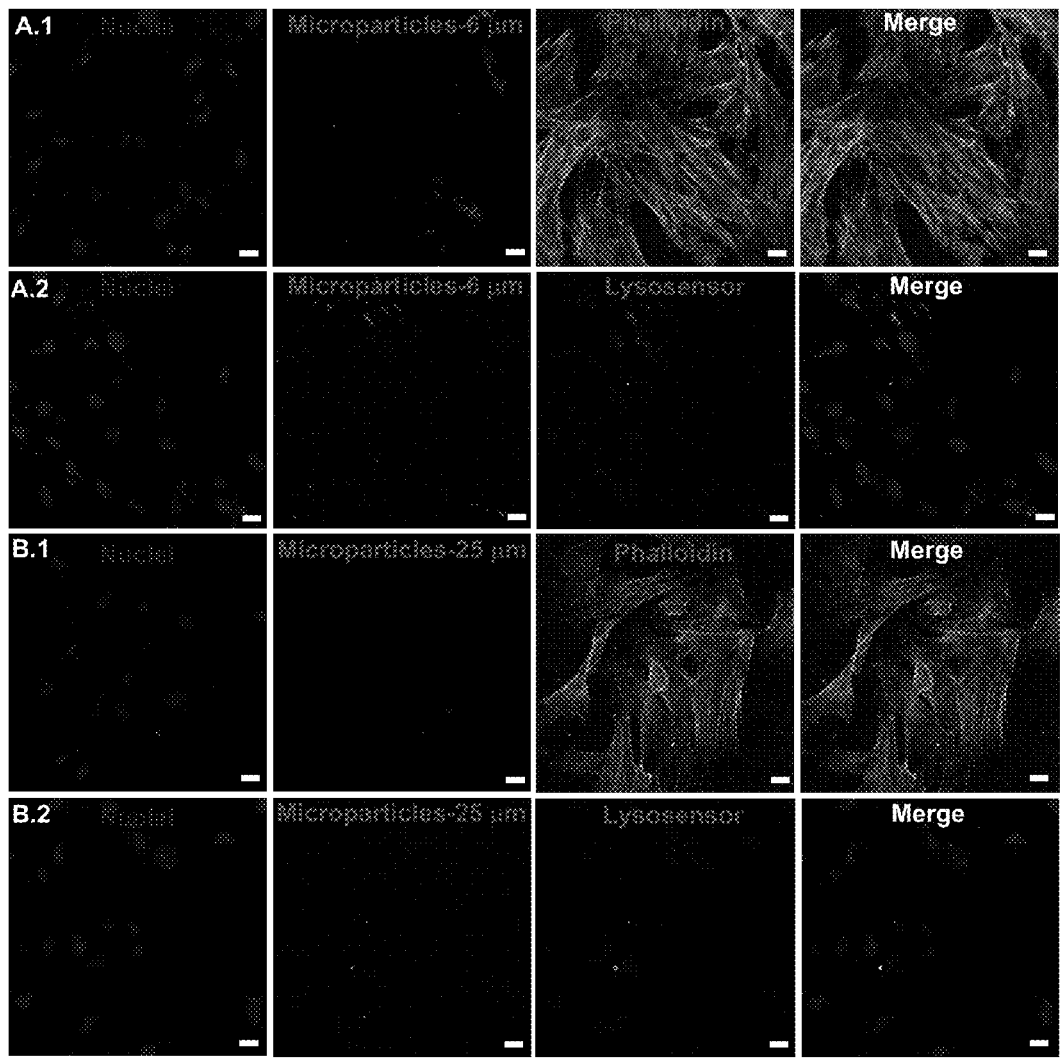
FIG. 7 illustrates cellular uptake of particles 6 (A) and 25 μm (B) as assessed by confocal microscopy. EBs were formed by the aggregation of 30,000 cells with 0.15 mg/mL particles, dissociated at day 2, plated for 18 h, washed thoroughly, and finally analyzed by confocal microscopy. Blue Topro-3 stains the nucleus, green lysosensor indicates endosomes (A.2 and B.2), green phalloidin indicates cytoplasm (A.1 and B.1), and TRITC-labeled particles are displayed in red. The small number of particles internalized by hESCs was observed within endosomes. Bar corresponds to 20 μm.

In various embodiments of the present inventions, methods of analyzing the location of the particles are provided. In various aspects, confocal microscopy was performed to confirm that PLGA particles were located intracellularly instead of adsorbing onto the cell surface and to identify the intracellular location following internalization. In general the method comprise the step of: (i) preparing EBs incorporating fluorescent-labeled particles, (ii) preparing a solution of embryoid bodies, and particles at a concentration of about 0.15 mg per mL of differentiation medium (iii) dissociating the cells at about day 2, (iv) plating the cells for about 18 hours, (v) fixing and then labeling the cells with either phalloidin to stain cellular actin, or lysoSensor green to stain endosomes (FIG. 2B), and (vi) examination under a confocal microscope. Images of hESCs reconstructed from z-stacks of confocal images indicated cellular uptake of particles with a mean size of 0.24 μm (FIG. 2B) and, in comparison, a lower uptake of particles with a mean size of 25 μm and particles with a mean size of 6 μm (FIG. 7). Particles taken up by hESCs were localized in the perinuclear region. Further information on the accumulation of materials in primary cells or mesenchymal stem cells may be found in References 14 and 15. Various aspects of the present inventions show that particles were localized in endosomes as shown by the co-localization of the particles with the lysoSensor green staining.

Regulatory factors that contribute to early vascular development include vascular endothelial growth factor ($VEGF_{165}$) [16], basic fibroblast growth factor (bFGF) [17] and placenta growth factor (PlGF) [18]. In various embodiments, $VEGF_{165}$ mediates its responses primarily by activating Flt-1 (also called VEGF-R1) and Flk-1/KDR (also called VEGF-R2) [19]. PlGF and bFGF mediate their effects through Flt-1 and FGF receptor tyrosine kinases, respectively [19]. The three receptors are expressed in EBs at early stages of differentiation and in some cases in undifferentiated hESCs [2, 20].

Other growth factors that may enhance the differentiation of vascular progenitor cells are: fibroblast growth factor (FGF), granulocyte-macrophage colony stimulating factor (GM-SCF), angiopoietin (Ang), ephrin (Eph), placental growth factor (PlGF), tumor growth factor, transforming growth factor ($\alpha$ or $\beta$-TGF), cytokines, erythropoietin, thrombopoietin, transferrin, insulin, stem cell factor (SCF), granulocyte colony-stimulating factor (G-CSF) and granulocyte-macrophage colony stimulating factor (GM-CSF), among others.

Figure 3:
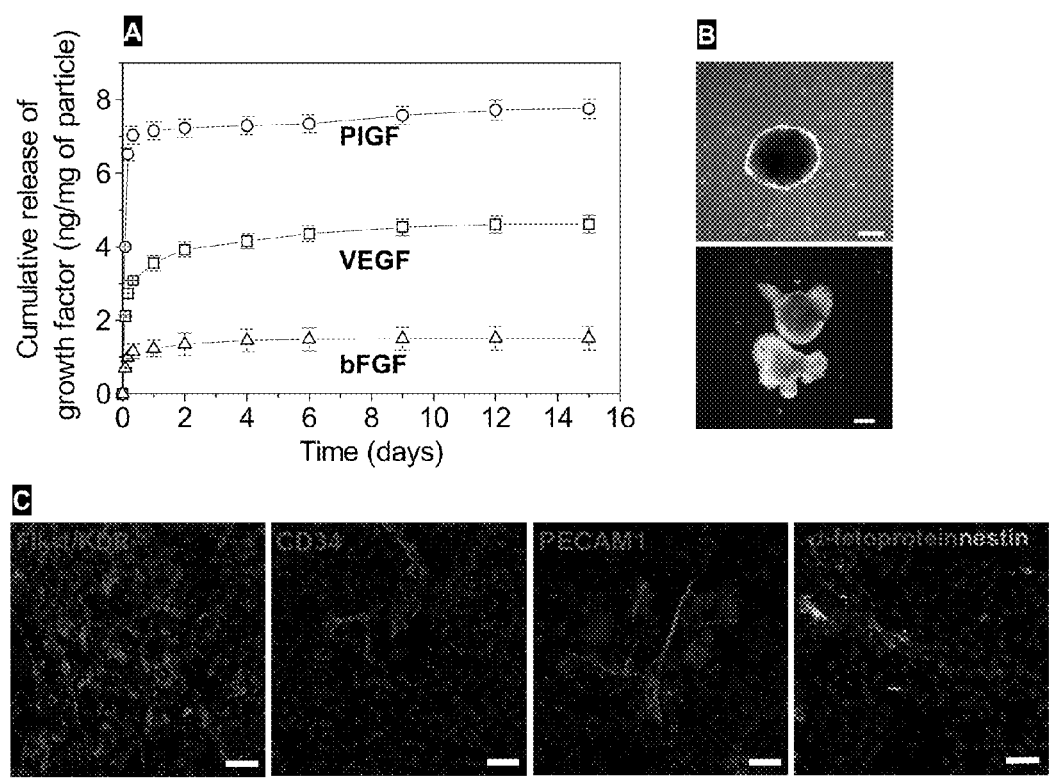
FIG. 3 illustrates growth-factor release in microparticles and protein expression in EBs containing growth factor-releasing microparticles. A) Release profile of $VEGF_{165}$, PlGF and bFGF. B) EBs at day 2 and 10 containing PlGF-releasing microparticles. Bar corresponds to 200 µm. C) Localization and organization of endothelial (Flk-1, CD34 and PECAM1) markers in EBs containing PlGF-releasing microparticles, as evaluated by confocal microscopy. Nestin/α-fetoprotein co-staining was also performed to assess the differentiation of EBs into the ectoderm and endoderm germ layers. Bar corresponds to 50 µm.

In various embodiments of the present inventions, growth factor release from the particles was extracellular. In various embodiments, particles of 6 μm in size were selected. In various embodiments, these particles remain extracellular, and they are dispersed in the composite EBs. The release kinetics of PLGA particles loaded with growth factors are shown in FIG. 3A. Quantitative differences in the cumulative mass of growth factor released from the particle preparations were observed (FIG. 3A and Table 2).

TABLE 2

Characteristics of growth factor-releasing microparticles.

| Microparticle characteristics | VEGF | bFGF | PlGF |
|---|---|---|---|
| Polymer inherent viscosity (dl/g) [a] | 0.16-0.24 | 0.16-0.24 | 0.16-0.24 |
| Particle size (μm) [b] | 9.49 ± 3.21 | 11.05 ± 3.89 | 11.51 ± 4.27 |
| Growth factor loading (ng) per mg of particles [c] | 50 | 50 | 50 |
| Experimental growth factor loading (ng) per mg of particles [d] | 43.2 | 29.5 | 38.5 |
| Growth factor released after 10 days (ng) [e] | ~4.5 | ~1.5 | ~7.6 |

[a] Information obtained by the manufacturer.
[b] Particle size was measured by a Coulter microparticle analyzer (Multisizer 3, Beckman Coulter, Miami, FL) (sample count: 50,000 microparticles).
[c] Theoretical mass of growth factor dispersed through 1 mg of particles. 2.5 mg of BSA, 5 μg of heparin and 4 mg of MgOH$_2$ were used per 100 mg of polymer.
[d] Mass of growth factor dispersed through 1 mg of particles assessed experimentally.
[e] Mass of growth factor released from 1 mg of microparticles placed in buffered saline for 10 days.

In various embodiments, the release kinetics of all three growth factor-loaded particles showed an initial release followed by a comparatively lower release rate. After about 10 days, about 1 mg of particles had released about 7.6, about 4.5 and about 1.5 ng of PlGF, VEGF and bFGF, respectively, corresponding to the release of about 20%, about 10% and about 5% of the initial amount of encapsulated growth factor. Previously, it has been shown that VEGF released from this particle formulation was functional, as assessed by a cell survival assay [21].

Figure 8:
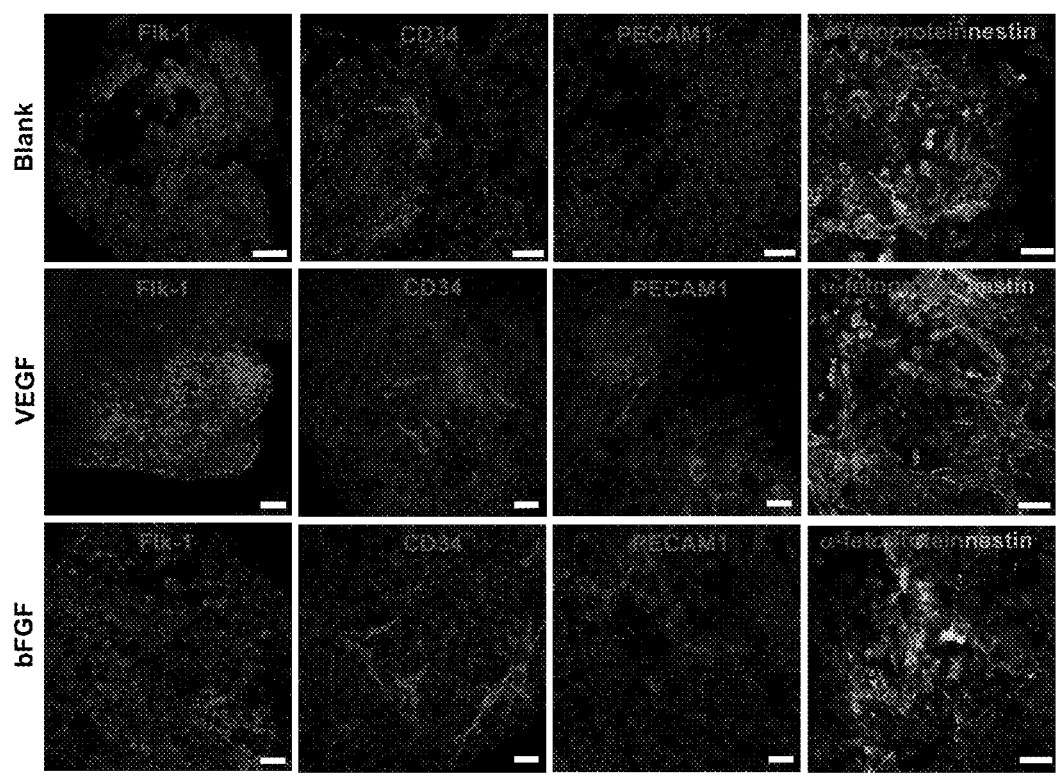
FIG. 8 illustrates localization and organization of endothelial (Flk-1, CD34 and PECAM1) markers in EBs containing bFGF, VEGF or blank (without growth factors) microparticles, at day 10, as evaluated by confocal microscopy. Nestin/α-fetoprotein co-staining was also performed to assess the differentiation of composite EBs into the ectoderm and endoderm germ layers. Bar corresponds to 50 μm.

In various embodiments growth factor-containing particles are incorporated in EBs for about 10 days (FIG. 3B). The vascular differentiation of the EBs was analyzed at both the protein and gene levels, and compared to constructs containing blank particles. For each EB about 25 μg of particles was used, which corresponds to about 195,000 particles as measured with a hemocytometer (see experimental section). Since about 70% of the particles initially used in each well were incorporated in the EBs, this corresponds to about 136,500 particles or a mass of about 17.5 μg per EB. In various embodiments, the genes and proteins analyzed included endothelial cell adhesion molecules including PECAM1, vascular endothelial-cadherin (VE-cad) and CD34; growth factor receptors including vascular endothelial growth factor receptor-2 (Flk-1/KDR) and Tie-2; endothelial glycoproteins including von Willebrand factor (vWF) and secreted endothelial molecules including angiopoietin 2 [3]. Immunofluorescence studies showed that of the three endothelial cell markers assessed (PECAM1, CD34 and Flk-1/KDR), Flk-1/KDR was expressed more often than the other two markers, in the conditions tested, about 40-50% of the cells displayed this marker (FIG. 3C and FIG. 8). In various embodiments, PECAM1 marker was more expressed in EBs with VEGF, PlGF and bFGF particles than with EBs without particles. FIG. 3C shows the localization and organization of endothelial markers in composite EBs containing PlGF particles. CD34$^+$ and PECAM1$^+$ cells seem to organize in vascular networks in regular EBs [2, 21] while KDR/Flk-1$^+$ cells are randomly organized. Similar results were obtained for the remaining composite EBs (FIG. 8).

Figure 4:
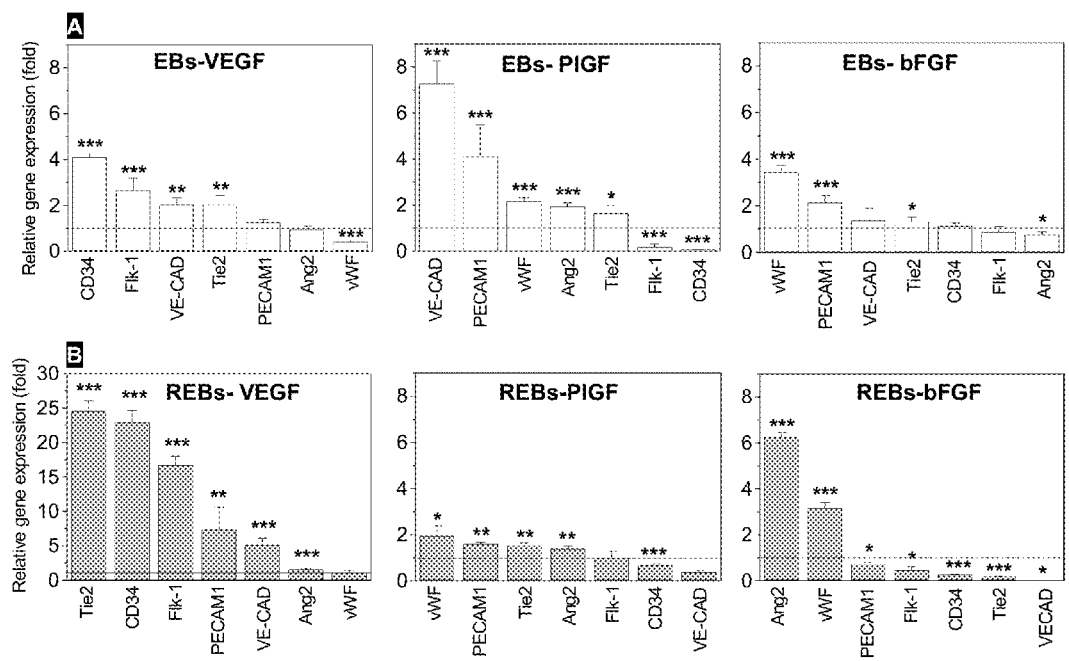
FIG. 4 illustrates endothelial differentiation on regular EBs or EBs containing growth factor-releasing microparticles. Endothelial gene expression in EBs containing growth factor-releasing microparticles (A; EBs) and regular EBs (B; REBs) as assessed by quantitative RT-PCR. REBs were formed by removing colonies of undifferentiated hESCs from the feeder layer and let them in suspension. EBs containing growth factor-releasing microparticles were formed by the forced aggregation of single hESCs and microparticles. In both cases, RNA was isolated at day 10 during differentiation and subjected to RT-PCR analysis. Quantification of target genes was performed relatively to the reference GAPDH gene, and normalized to the expression of the different markers in EBs with blank particles or REBs cultured without growth factors. *,  and * denote statistical significance (P<0.05, P<0.01 and P<0.001, respectively).

In various embodiments, differentiation of EBs can be evaluated at the gene level. In various embodiments of the present inventions, VEGF, PlGF and bFGF particles facilitate vascular differentiation of EBs, as 3-5 of the 7 genes are up-regulated as compared to EBs containing blank particles (FIG. 4A). In various embodiments, PlGF facilitated a comparatively greater effect than the other two growth factors under the conditions tested. In various embodiments, the gene expression of EBs containing growth factor-releasing particles and EBs formed by the removal of hESC colonies from a feeder layer and exposed to medium supplemented with each of growth factors (about 50 ng/mL) for about 10 days (FIG. 4B) were compared. In various embodiments, although EBs containing bFGF or PlGF particles were exposed to lower concentrations of growth factors than EBs exposed to exogenous factors (for bFGF about 175 pg/mL versus about 50 ng/mL and for PlGF about 887 pg/mL versus about 50 ng/mL) the vascular differentiation was comparable. For example, the expression of PECAM-1, a definitive marker for endothelial cells [2, 17], was about 2 or about 4-fold higher in EBs containing bFGF or PlGF particles than regular EBs exposed to those growth factors, respectively. Without being bound by any particular theory, the release of growth factors by particles within EBs facilitated vascular differentiation of the EBs.

Figure 9:
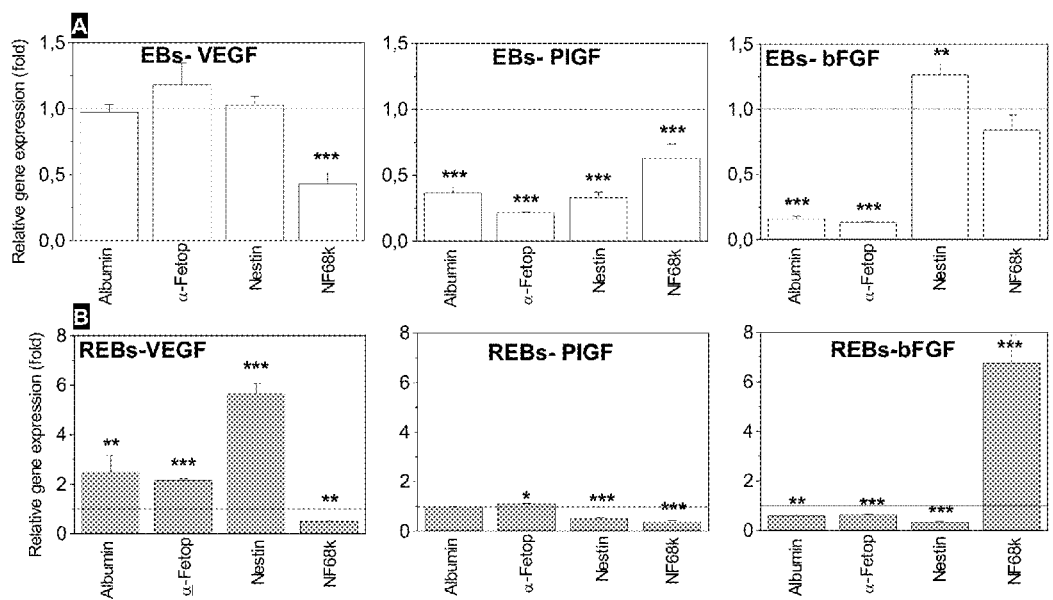
FIG. 9 illustrates ectodermal and endodermal differentiation in regular EBs or EBs containing growth factor-releasing microparticles. Albumin and α-fetoprotein (α-Fetop) are genes for endodermal differentiation while nestin and neurofilament 68k (NF68k) are genes for ectodermal differentiation. Gene expression in EBs incorporating growth factor-releasing microparticles (A; EBs) and regular EBs (B; REBs) as assessed by quantitative RT-PCR. Regular EBs were formed by removing colonies of undifferentiated hESCs from the feeder layer and let them in suspension. EBs containing growth factor-releasing microparticles were formed by the forced aggregation of single hESCs and microparticles containing different growth factors. In both cases, RNA was isolated at day 10 during differentiation and subjected to RT-PCR analysis. Quantification of target genes was performed relatively to the reference GAPDH gene, and normalized to the expression of the different markers in EBs with blank particles or REBs cultured without growth factors. *,  and * denote statistical significance (P<0.05, P<0.01 and P<0.001, respectively).
Figure 10:
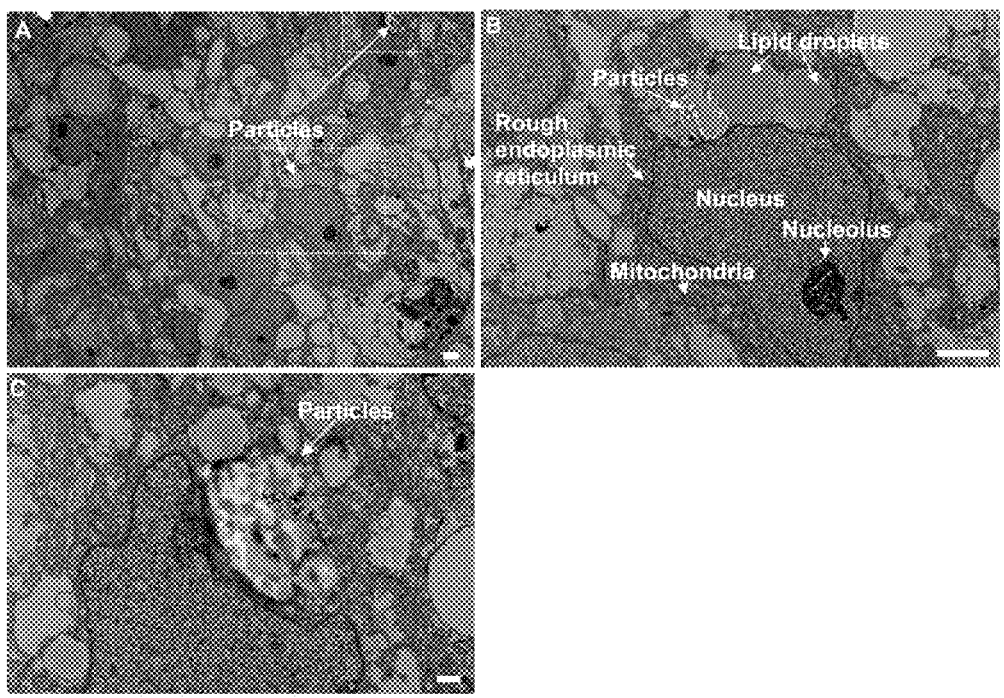
FIG. 10 illustrates an electron micrographs of EBs containing nanoparticles at day 2. High magnification of the area defined by the dashed square is shown in B. Nanoparticles were taken up by cells and accumulate in the perinuclear region. Bar corresponds to 2 μm

In various aspects, the growth factor-releasing particles in EBs can effect the differentiation toward other germ layers (i.e., ectoderm and endoderm germ layers). The expression of genes and proteins related to neuronal differentiation (ectodermal differentiation) including nestin and neurofilament 68 Kd [4, 7, 21], and markers related to hepatic differentiation (endodermal differentiation) including albumin and α-fetoprotein [7, 21] was evaluated. In various aspects, PlGF particles in EBs reduced the neuronal and hepatic differentiation of cells as compared to EBs containing blank particles (FIG. 3C and FIG. 9), and this effect was greater than in regular EBs exposed to PlGF. In various embodiments, bFGF particles in EBs reduced the hepatic but not the neuronal differentiation, while VEGF particles incorporated in EBs have no effect in the hepatic differentiation and variable effect in the neuronal differentiation.

EXAMPLES

The present examples provide experimental data on the use of micro- and nanoparticles in the delivery of growth factor for embryoid body differentiation, according to the various embodiments of the present inventions.

Preparation of Growth Factor-Releasing Particles:

Particles were Prepared Using a double emulsion solvent evaporation procedure. For nanoparticles, PLGA (100 mg, inherent viscosity 0.16-0.24 dl/g, Boheringer Manheim) polymer was dissolved in ethyl acetate (1 mL, Aldrich) with magnesium hydroxide (4 mg, Aldrich). Then, 50 µL of an aqueous solution of BSA (50 mg/mL BSA in 10 mM phosphate buffer, pH 7.4 containing 5 µg of heparin) was added to the organic polymer solution, and the aqueous and organic phases were emulsified by sonication (Vibra Cell, Sonics & Materials, Inc., Danbury, Conn.). For microparticles 6 and 25 µm, PLGA (100 mg, inherent viscosities of 0.16-0.24 or 0.32-0.44 dl/g) polymer (see Table 1) was dissolved in methylene chloride (2 ml, Aldrich) with magnesium hydroxide (4 mg). Then, 50 µl of PlGF or bFGF or $VEGF_{165}$ (R&D Systems) (5 µg; in 50 mg/mL BSA in 10 mM phosphate buffer, pH 7.4 containing 5 µg of heparin) or BSA solution was added to the organic polymer solution, and the aqueous and organic phases were emulsified by sonication (Vibra Cell, Sonics & Materials, Inc., Danbury, Conn.). For the preparation of fluorescence-labeled particles, 20 mL of a tetramethyl-rhodamine-5-(and-6)-isothiocyanate (TRITC; Molecular Probes; 10 mg/mL in ethyl acetate or methylene chloride) was added to the organic phase of each formulation, maintaining the other components. Microparticles and nanoparticles were prepared and characterized as previously described [23] and stored at −20° C. The morphology of PLGA particles during growth factor release was evaluated by scanning electron microscopy (SEM). For that purpose, they were mounted onto an aluminum stud, and gold coated by plasma vapor deposition. To determine the density of particles 6 µm, 2.5 mg of microparticles were suspended in 1.25 mL of PBS after which a small volume of this solution was loaded into a hemocytometer, visualized using a phase contrast microscope (40×), and counted. This procedure was repeated for at least two different batches to yield an overall estimate of $7.8 \times 10^6$ (±9.5% S.D.) microparticles/mg powder.

Growth Factor Release Studies:

Microparticles (10 mg) were placed in PBS (0.5 mL) and incubated under mild agitation, at 37° C. At specific intervals of time, the particle suspension was centrifuged (at 4,000 rpm for 2 min) and 0.4 mL of the release medium removed and replaced by a new one. The reserved supernatant was stored at −20° C. until the growth factor content in release samples was assessed using an enzyme-linked immunosorbent assay (ELISA) (R&D Systems). Concentrations of growth factors were determined by comparison to a standard curve. All analyses were conducted in duplicate. To determine the loading efficiency of PLGA particles, 2.5 mg of microparticles were dissolved in 0.5 mL of 1 N NaOH overnight and the absorbance measured at 284 nm. The results are expressed as a percentage of the ratio of protein encapsulated to total protein used.

hESC Culture and Formation of EBs:

Undifferentiating hESCs (H9, passages 25 to 50; WiCell, Wis.) were grown on an inactivated mouse embryonic fibroblast (MEF) feeder layer, as previously described [2, 21]. To induce the formation of EBs, undifferentiated hESCs were treated with 2 mg/mL type IV collagenase for 1-2 h, and then transferred (2:1) to low attachment plates (diameter=10 cm, Corning) containing 10 mL of differentiation medium [80% knockout-Dulbecco's Modified Eagle Medium, supplemented with 20% fetal bovine serum (FBS, Invitrogen), 0.5% L-glutamine, 0.2% β-mercaptoethanol and 1% nonessential amino acids (all from Invitrogen)]. The EBs obtained by this procedure are named regular EBs. They were cultured for 10 days at 37° C. and 5% $CO_2$ in a humidified atmosphere, with changes of media every 2-3 days. To assess the effect of bFGF, PlGF and $VEGF_{165}$ in the differentiation profile of EBs, the differentiation medium was supplemented with 50 $ngmL^{-1}$ of growth factor.

Preparation of Ebs Containing Nano- and Microparticles:

Undifferentiated hESCs seeded on MEFS were treated with 2 mg/mL type IV collagenase for 2 h, washed in PBS, then treated with cell dissociation solution for 10 minutes and dissociated by gentle pipetting. EB formation was induced by seeding a sufficient number of hESCs in 168.5 µL of differentiation medium containing 0.15 or 0.06 or 0.03 mg/mL of particles in each well of 96-well plate, round-bottomed, low-attachment plates (Nunc, Denmark). The plates were then centrifuged at 1,200 rpm for 4 minutes to aggregate the cells. At day 2, the formed EBs were removed from the 96 well-plate and placed in a low-adherent 24 well-plate (4-6 EBs per well). The differentiation medium was changed every 2-3 days.

Viability and Metabolic Activity of EBs Containing Particles:

Cell viability of EBs containing particles was determined using a LIVE/DEAD kit (Molecular Probes) containing calcein AM (2 µg/mL, in PBS) and ethidium homodimer (4 µg/mL, in PBS). The EBs were placed in the kit solution for 20 min and visualized under a Zeiss LSM 510 confocal microscope. This kit measures the membrane integrity of cells. Viable cells fluoresce green through the reaction of calcein AM with intracellular esterase, whereas non-viable cells fluoresce red due to the diffusion of ethidium homodimer across damaged cell membranes and binding with nucleic acids.

The metabolic activity of EBs containing particles was measured through a MTT assay after 2 and 10 days of culture. The MTT solution (0.2 mL, 0.45 mg/mL in differentiation medium) was added to each well (96 well-plate) containing ca. 6 EBs for 3 h, at 37° C. After that time, the medium was removed and 0.1 mL of DMSO was added for 15 min. The absorbance was then measured spectrophotometrically at 540 nm.

FACS Analysis:

EBs differentiated for 2 days were treated with trypsin (0.25% in PBS) for 5 minutes and dissociated by gentle pipetting. Single cells were plated in a 1% gelatin-coated 24 well plate ($1 \times 10^5$ cells/well) containing differentiation medium. After 18 h, the cells were washed with PBS and dissociated with trypsin. The single cell suspensions were then analyzed on a FACScan (Becton Dickison), using a CellQuest software.

Confocal Microscopy Analysis:

At day 10 of differentiation, EBs containing particles were transferred to gelatin-coated cover slips with differentiation medium, allowed to attach overnight, and then, fixed with 4% (w/v) paraformaldehyde for 30 minutes at room temperature. To evaluate the distribution of TRITC-labeled particles within EBs, the cell nuclei were stained with Topro-3 (Sigma) followed by the examination with a Zeiss LSM 510 confocal microscope.

To evaluate endothelial marker expression in EBs containing growth factor-releasing particles, fixed EBs were blocked with 3% BSA solution, and the cells stained for 1 h with the following anti-human primary antibodies: PECAM1 (Dako), CD34 (Dako), Flk-1/KDR (Santa Cruz Biochemicals), nestin (R&D Systems) and α-fetoprotein (Dako). In each experiment, an isotype-matched IgG control was used. Binding of primary antibodies to specific cells was detected with anti-mouse IgG Cy3 conjugate, anti-rabbit IgG Cy3 conjugate or anti-mouse IgG FITC (all from Sigma). Cell nuclei were stained with Topro-3 and the slides examined by confocal microscopy.

To evaluate the cellular uptake of particles, EBs containing particles and differentiated for 2 days were dissociated by trypsin (0.25% in PBS) and plated ($1\times10^5$ cells/well) in a 1% gelatin-coated chamber slides containing differentiation medium for 18 h. For lysosensor staining, cells were stained with lysosensor green (2 μM in differentiation medium; Molecular Probes) for 1 h, washed with PBS, and then fixed with 4% (w/v) paraformaldehyde for 15 minutes at room temperature. Cell nuclei were stained with Topro-3 (0.002%, v/v, in PBS) for 30 min. For phalloidin staining, cells were fixed with 4% (w/v) paraformaldehyde for 15 minutes at room temperature, washed with PBS, permeabilized with 0.1% Triton X-100 in PBS, washed again with PBS and finally stained with 50 μg/mL FITC-phalloidin (Sigma) for 30 minutes at room temperature. The stained cells were then washed with PBS and cell nuclei stained with Topro-3.

Reverse Transcription-Polymerase Chain Reaction (RT-PCR) Analysis:

Total RNA from regular EBs or EBs containing microparticles (3-4 separate experiments and combined in equal amounts) was isolated with RNeasy Minikit (Qiagen, Valencia). cDNA was prepared from 1 mg total RNA using Taqman Reverse transcription reagents (Applied Biosystems, CA). Quantitative PCR (qPCR) was performed using Power SYBR Green PCR Master Mix (Applied Biosystems) and the detection using a 7500 Fast Real-Time PCR System (Applied Biosystems, Foster). Quantification of target genes was performed relatively to the reference GAPDH gene: relative expression=$2^{[-(Ct_{sample}-Ct_{GADPH})]}$. The mean minimal cycle threshold values (Ct) were calculated from quadruplicate reactions. Then, the relative gene expression for EBs containing growth factor-releasing microparticles was normalized to the relative gene expression found in EBs containing blank particles. Primer sequences are published as supporting information (Table 3).

TABLE 3

Primer sequences used for RT-PCR analyses [a].

| Cell type | Gene transcript | Primer sequences (5' to 3', $F_w$/$R_v$) | Product (bp) |
|---|---|---|---|
| Endothelial | PECAM1 | GCTGTTGGTGGAAGGAGTGC GAAGTTGGCTGGAGGTGCTC (SEQ ID: 1) | 620 |
| Endothelial | CD34 | TGAAGCCTAGCCTGTCACCT CGCACAGCTGGAGGTCTTAT (SEQ ID: 2) | 200 |
| Endothelial | KDR/Flk-1 | CTGGCATGGTCTTCTGTGAA GCAAATACCAGTGGATGTGA TGGCGG (SEQ ID: 3) | 790 |
| Endothelial | Angiopoietin-2 | GGATCTGGGGAGAGAGGAAC CTCTGCACCGAGTCATCGTA (SEQ ID: 4) | 535 |
| Endothelial | Tie2 | ATCCCATTTGCAAAGCTTCT GGCTGGCTGTGAAGCGTCTC ACAGGTCCAGGATG (SEQ ID: 5) | 512 |
| Endothelial | VE-cad | ACGGGATGACCAAGTACAGC ACACACTTTGGGCTGGTAGG (SEQ ID: 6) | 596 |
| Endothelial | Von Willebrand Factor (vWF) | ATGTTGTGGGAGATGTTTGC GCAGATAAGAGCTCAGCCTT (SEQ ID: 7) | 656 |
| Household gene | GAPDH | AGCCACATCGCTCAGACACC GTACTCAGCGCCAGCATCG (SEQ ID: 8) | 302 |
| Neuronal | Neurofilament 68 Kd | GAGTGAAATGGCACGATACC TATTTCCTCTCCTTCTTCAC CTTC (SEQ ID: 9) | 473 |
| Neuronal | Nestin | AGAGGGGAATTCCTGGAGCT GAGGACCAGGACTCTCTA (SEQ ID: 10) | 497 |
| Hepatocyte | Albumin | TGCTTGAATGTGCTGATGAC AGGGAAGGCAAGTCAGCAGC CATCTCAT (SEQ ID: 11) | 157 |

TABLE 3-continued

Primer sequences used for RT-PCR analyses [a].

| Cell type | Gene transcript | Primer sequences (5' to 3', F$_w$/R$_v$) | Product (bp) |
|---|---|---|---|
| Hepatocyte | α-fetoprotein | GCTGGATTGTCTGCAGGATG GGGAATCCCCTGAAGAAAAT TGGTTAAAAT (SEQ ID: 12) | 216 |

[a] PCR conditions consisted of the following: 2 minutes at 50° C. and 10 seconds at 95° C. (activation), 40 cycles, 15 seconds at 95° C. (denaturation), and 60 seconds at 60° C. (annealing/extension).

Statistical Analysis:

An unpaired t test or one-way analysis of variance with Bonferroni post test was performed for statistical tests by using GraphPad Prism 4.0 (San Diego, Calif.). Results were considered significant when P≤0.05.

EQUIVALENTS

The foregoing has been a description of certain non-limiting embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

INCORPORATION BY REFERENCE

All publications and patent documents cited in this application are incorporated by reference in their entirety for all purposes to the same extent as if the contents of each individual publication or patent document were incorporated herein.

REFERENCES

[1] L. M. Hoffman, M. K. Carpenter, *Nat Biotechnol* 2005, 23, 699.
[2] L. S. Ferreira, S. Gerecht, H. F. Shieh, N. Watson, M. A. Rupnick, S. M. Dallabrida, G. Vunjak-Novakovic, R. Langer, *Circ Res* 2007.
[3] S. Levenberg, J. S. Golub, M. Amit, J. Itskovitz-Eldor, R. Langer, *Proc Natl Acad Sci U S A* 2002, 99, 4391.

[4] S. C. Zhang, M. Wernig, I. D. Duncan, O. Brustle, J. A. Thomson, *Nat Biotechnol* 2001, 19, 1129.
[5] E. Poon, F. Clermont, M. T. Firpo, R. J. Akhurst, *J Cell Sci* 2006, 119, 759.
[6] C. M. Cameron, W. S. Hu, D. S. Kaufman, *Biotechnol Bioeng* 2006, 94, 938.
[7] S. Gerecht-Nir, S. Cohen, J. Itskovitz-Eldor, *Biotechnol Bioeng* 2004, 86, 493.
[8] E. R. Edelman, M. A. Nugent, M. J. Karnovsky, *Proc Natl Acad Sci USA* 1993, 90, 1513.
[9] M. J. Mahoney, W. M. Saltzman, *Nat Biotechnol* 2001, 19, 934.
[10] E. S, Ng, R. P. Davis, L. Azzola, E. G. Stanley, A. G. Elefanty, *Blood* 2005, 106, 1601.
[11] K. Y. Win, S. S. Feng, *Biomaterials* 2005, 26, 2713.
[12] M. P. Desai, V. Labhasetwar, E. Walter, R. J. Levy, G. L. Amidon, *Pharm Res* 1997, 14, 1568.
[13] B. D. Chithrani, A. A. Ghazani, W. C. Chan, *Nano Lett* 2006, 6, 662.
[14] L. Lacerda, G. Pastorin, D. Gathercole, J. Buddle, M. Prato, A. Bianco, K. Kostarelos, *Advanced Materials* 2007, 19, 1480.
[15] O. Seleverstov, O. Zabirnyk, M. Zscharnack, L. Bulavina, M. Nowicki, J. M. Heinrich, M. Yezhelyev, F. Emmrich, R. O'Regan, A. Bader, *Nano Lett* 2006, 6, 2826.
[16] P. Carmeliet, V. Ferreira, G. Breier, S. Pollefeyt, L. Kieckens, M. Gertsenstein, M. Fahrig, A. Vandenhoeck, K. Harpal, C. Eberhardt, C. Declercq, J. Pawling, L. Moons, D. Collen, W. Risau, A. Nagy, *Nature* 1996, 380, 435.
[17] D. Vittet, M. H. Prandini, R. Berthier, A. Schweitzer, H. Martin-Sisteron, G. Uzan, E. Dejana, *Blood* 1996, 88, 3424.
[18] P. Carmeliet, L. Moons, A. Luttun, V. Vincenti, V. Compemolle, M. De Mol, Y. Wu, F. Bono, L. Devy, H. Beck, D. Scholz, T. Acker, T. DiPalma, M. Dewerchin, A. Noel, I. Stalmans, A. Barra, S. Blacher, T. Vandendriessche, A. Ponten, U. Eriksson, K. H. Plate, J. M. Foidart, W. Schaper, D. S. Charnock-Jones, D. J. Hicklin, J. M. Herbert, D. Collen, M. G. Persico, *Nat Med* 2001, 7, 575.
[19] H. Roy, S. Bhardwaj, S. Yla-Herttuala, *FEBS Lett* 2006, 580, 2879.
[20] M. Schuldiner, O. Yanuka, J. Itskovitz-Eldor, D. A. Melton, N. Benvenisty, *Proc Natl Acad Sci USA* 2000, 97, 11307.
[21] L. S. Ferreira, S. Gerecht, J. Fuller, H. F. Shieh, G. Vunjak-Novakovic, R. Langer, *Biomaterials* 2007, 28, 2706.
[22] E. N. Olson, *Nat Med* 2004, 10, 467.
[23] B. A. Pfeifer, J. A. Burdick, R. Langer, *Biomaterials* 2005, 26, 117. [24] L. M. Hoffman, M. K. Carpenter, Nature Biotechnology 2005, 23(6), 699-708)

In accordance with 37 CFR 1.52(e)(5), a Sequence Listing in the form of a text file (entitled "MIT12873 SequenceListing.txt," created on Jun. 24, 2009, and 6 kilobytes) is incorporated herein by reference in its entirety.

What is claimed is:

1. A method of directing differentiation of stem cells comprising the steps of:
   providing human embryonic stem cells;
   providing microparticles with a diameter in the range of between about 0.2 μm and about 6 μm, wherein the microparticles comprise a growth factor;
   contacting the embryonic stem cells with the microparticles, in a solution, under conditions suitable to form aggregates comprising the embryonic stem cells and the microparticles and to affect differentiation of the cells in the formation of the embryoid bodies.

2. The method of claim 1 wherein the contacting step comprises centrifuging the mixture of cells and microparticles.

3. The method of claim 1 wherein the microparticles are comprised of a bio-compatible and biodegradable polymer.

4. The method of claim 3 wherein the polymer comprises poly(lactide-co-glycolide).

5. The method of claim 3 wherein the microparticles are comprised of a material selected from the group comprising poly(anhydrides), poly(hydroxy acids), poly(ortho esters), poly(propylfumerates), poly(caprolactones), polyamides, polyamino acids, polyacetals, biodegradable polycyanoacrylates, biodegradable polyurethanes, poly(glycerol sebacates), elastomeric poly(glycerol sebacates polysaccharides), and combinations thereof.

6. The method of claim 1 wherein the microparticles are comprised of a material selected from the group comprising polypyrrole, polyanilines, polythiophene, polystyrene, polyesters, non-biodegradable polyurethanes, polyureas, poly (ethylene vinyl acetate), polypropylene, polymethacrylate, polyethylene, polycarbonates, poly(ethylene oxide), co-polymers and combinations thereof.

7. The method of claim 1 wherein the microparticles comprise VEGF165 as the growth factor and the cells, after contacting with the microparticles, express CD 34.

8. The method of claim 1 wherein the microparticles comprise PlGF and/or bFGF as the growth factor and the cells, after contacting with the microparticles, express PECAM1.

9. The method of claim 1 wherein the growth factor is selected from the group consisting of vascular endothelial growth factor (VEGF165), basic fibroblast growth factor (bFGF), placenta growth factor (PlGF), and combinations thereof.

10. The method of claim 1 wherein the growth factor is selected from the group comprising epidermal growth factor, nerve growth factor, transforming growth factor-β, platelet-derived growth factor, insulin-like growth factor, acidic fibroblast growth factor, basic fibroblast growth factor, hepatocyte growth factor, brain-derived neurotrophic factor, keratinocyte growth factor, bone morphogenetic protein, a cartilage-derived growth factor, and combinations thereof.

11. The method of claim 1 wherein the microparticles may be taken up by the cells of the embryoid bodies.

12. The method of claim 1 wherein the first providing step comprises providing about 30,000 stem cells.

* * * * *